United States Patent
Beard et al.

[11] 3,993,768
[45] *Nov. 23, 1976

[54] 5(6)-BENZENE RING SUBSTITUTED BENZIMIDAZOLE-2-CARBAMATE DERIVATIVES HAVING ANTHELMINTIC ACTIVITY

[75] Inventors: Colin C. Beard, Palo Alto; John A. Edwards, Los Altos; John H. Fried, Palo Alto, all of Calif.

[73] Assignee: Syntex (U.S.A.) Inc., Palo Alto, Calif.

[ * ] Notice: The portion of the term of this patent subsequent to Dec. 30, 1992, has been disclaimed.

[22] Filed: Aug. 13, 1975

[21] Appl. No.: 604,502

Related U.S. Application Data

[60] Division of Ser. No. 526,861, Nov. 25, 1974, Pat. No. 3,929,824, which is a continuation-in-part of Ser. No. 417,963, Nov. 21, 1973, Pat. No. 3,929,821, which is a continuation-in-part of Ser. No. 319,299, Dec. 29, 1972, abandoned.

[52] U.S. Cl. .............................. 424/273; 260/309.2
[51] Int. Cl.² ........................................ C07D 235/32
[58] Field of Search .................. 260/309.2; 424/273

[56] References Cited
UNITED STATES PATENTS
| | | | |
|---|---|---|---|
| 3,574,845 | 4/1971 | Actor .............................. | 260/309.2 |
| 3,694,455 | 9/1972 | Dunn .............................. | 260/309.2 |
| 3,929,822 | 12/1975 | Beard et al. ...................... | 260/309.2 |

FOREIGN PATENTS OR APPLICATIONS
| | | | |
|---|---|---|---|
| 1,114,069 | 5/1968 | United Kingdom .............. | 260/309.2 |

*Primary Examiner*—Natalie Trousoe
*Attorney, Agent, or Firm*—Joseph I. Hirsch; William B. Walker

[57] ABSTRACT

This application describes further species embraced by the following generic formula:

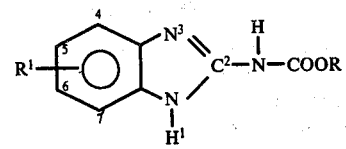

where R is a lower alkyl group having 1 to 4 carbon atoms; $R^1$ is $-SOR^2$, $-SO_2R^2$, $-SCN$, $-SR^5$, $-OR^5$ or $M'(CH_2)_nMR^7$ where M and M' are independently

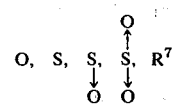

is lower alkyl having 1 to 4 carbon atoms or aryl, and $n$ is 1–4; $R^2$ is lower alkyl having from 1 to 6 carbon atoms, cycloalkyl having 3 to 7 carbon atoms, lower alkenyl or lower alkynyl having 3 to 6 carbon atoms, or aralkyl or aryl; $R^5$ is lower alkenyl, lower alkynyl, or aralkyl; and the $R^1$ substitution is at the 5(6)-position. The above compounds can also be substituted at the 1-position.

14 Claims, No Drawings

5(6)-BENZENE RING SUBSTITUTED BENZIMIDAZOLE-2-CARBAMATE DERIVATIVES HAVING ANTHELMINTIC ACTIVITY

REFERENCE TO PARENT APPLICATIONS

This application is a division of application Ser. No. 526,861, filed Nov. 25, 1974, now U.S. Pat. No. 3,929,824, which, in turn, is a continuation-in-part application of application Ser. No. 417,963, filed Nov. 21, 1973, now U.S. Pat. No. 3,929,821, which, in turn, is a continuation-in-part application of application Ser. No. 319,299, filed Dec. 29, 1972, now abandoned.

FIELD OF THE INVENTION

This invention relates to novel chemical compounds. More particularly, this invention relates to novel anthelmintically active benzimidazole-2-carbamate derivatives wherein the benzene ring is substituted at the 5(6)-position.

BACKGROUND OF THE INVENTION

In application Ser. No. 417,963, filed Nov. 21, 1973, now U.S. Pat. No. 3,929,821, which is a continuation-in-part of application Ser. No. 319,299, filed Dec. 29, 1972, now abandoned, there are described novel benzene ring substituted benzimidazole-2-carbamate derivatives represented by the following formula:

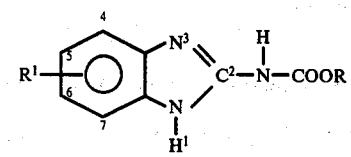

where R is a lower alkyl group having 1 to 4 carbon atoms; $R^1$ is $-SOR^2$, $-SO_2R^2$, $-SCN$, $-SR^5$, $-OR^5$ or $M'(CH_2)_nMR^7$ where M and M' are independently O, S,

$R^7$ is lower alkyl having 1 to 4 carbon atoms or aryl, and n is 1–4; $R^2$ is a lower alkyl having from 1 to 6 carbon atoms, cycloalkyl having 3 to 7 carbon atoms, lower alkenyl, or lower alkynyl having 3 to 6 carbon atoms, or aralkyl or aryl; $R^5$ is lower alkenyl, lower alkynyl or aralkyl; and the $R^1$ substitution is at the 5(6)-position.

As stated therein, the term "lower alkyl" referred to both straight and branched chain alkyl groups having either a total of from 1 through 4 carbon atoms or from 1 through 6 carbon atoms, and thus included primary, secondary and tertiary alkyl groups. Typical lower alkyls included, for example, methyl, ethyl, n-propyl, isopropyl, n-butyl, isobutyl, t-butyl, n-amyl, n-hexyl and the like. The term "cycloalkyl" referred to cyclic hydrocarbon groups having from 3 to 7 carbon atoms such as, for example, cyclopropyl, cyclopentyl, cyclo-hexyl, and the like. The term "lower alkenyl" referred to an unsaturated hydrocarbon group having from 3 to 6 carbon atoms and a single carbon-carbon double bond, provided that the double bond was not on the α-carbon atom. Typical alkenyl groups included, for example, 2-propenyl, 2-butenyl, 3-butenyl, and the like. The term "lower alkynyl" referred to an unsaturated hydrocarbon group having from 3 to 6 carbon atoms, and a single carbon-carbon triple bond, provided also that the triple bond was not on the α-carbon atom. Typical alkynyl groups included, for example, 2-propynyl, 2-butenyl, 3-butynyl, and the like. It was stated that an alkyl, alkenyl or alkynyl group of the $R^1$ moiety could be optionally substituted with one or more radicals, for example, thiocyanato; alkoxy, such as methoxy; aryl, such as phenyl; aroyl, such as benzoyl; hydroxy; cycloalkyl; halo; cyano; or nitro radicals. The term "alkoxy" referred to the group having the formula RO— wherein R is a lower alkyl as defined above. Typical alkoxy groups included, for example, methoxy, ethoxy, t-butoxy and the like. The term "halo" referred to iodo, bromo, chloro and fluoro groups. The term "aryl" referred to an aromatic hydrocarbon group, such as phenyl. The term "aralkyl" referred to an aryl substituted alkyl group, such as, for example, benzyl of phenethyl. The term "aroyl" referred to the group having the formula $$R'C- \atop \|  \atop O$$

where R' is an aryl group. The aryl or aralkyl groups could be optionally substituted with one or more lower alkyl, alkoxy, halo, nitro, cyano, thiocyanato, isothiocyanato, trifluoromethyl, alkylthio, alkylsulfinyl, alkylsulfonyl, acyl or acylamino where the acyl portion has 1 to 6 carbon atoms, $-SO_2NR^3R^4$ or $-N(R^3)SO_2R^4$ radicals; where $R^3$ and $R^4$ are independently hydrogen or lower alkyl having 1 to 6 carbon atoms. The terms "alkylthio", "alkylsulfinyl", and "alkylsulfonyl" referred to those groups having the formula RS-, $$RS- \atop \downarrow \atop O$$

and $$O \atop \uparrow \atop RS- \atop \downarrow \atop O$$

respectively, where R is a lower alkyl (1–6C) as defined above. The term "acyl" referred to acyl groups derived from carboxylic acids having 1 through 6 carbon atoms such as acetyl, propionyl, butyryl, valeryl, isovaleryl, hexanoyl and the like.

SUMMARY OF THE INVENTION

This application describes further compounds embraced by formula I above. They are as follows:

5(6)-(3-chloropropylsulfinyl)-2-carbomethoxyaminobenzimidazole;
5(6)-(3-bromopropylsulfinyl)-2-carbomethoxyaminobenzimidazole;
5(6)-(3-hydroxypropylsulfinyl)-2-carbomethoxyaminobenzimidazole;
5(6)-(2,2-dichloroethylsulfinyl)-2-carbomethoxyaminobenzimidazole;
5(6)-(3-phenyl-prop-2-en-1-ylthio)-2-carbomethoxyaminobenzimidazole;
5(6)-(3-phenyl-prop-2-en-1-ylsulfinyl)-2-carbomethoxyaminobenzimidazole;
5(6)-(3-chloro-prop-2-en-1-ylthio)-2-carbomethoxyaminobenzimidazole;
5(6)-(3-chloro-prop-2-en-1-ylsulfinyl)-2-carbomethoxyaminobenzimidazole;
5(6)-(2,3-dichloro-prop-2-en-1-ylthio)-2-carbomethoxyaminobenzimidazole;
5(6)-(2,3-dichloro-prop-2-en-1-ylsulfinyl)-2-carbomethoxyaminobenzlmidazole;
5(6)-(2-chloro-prop-2-en-1-ylthio)-2-carbomethoxyminobenzimidazole;
5(6)-(2-chloro-prop-2-en-1-ylsulfinyl)-2-carbomethoxyaminobenzimidazole;
5(6)-(but-3-en-1-ylthio)-2-carbomethoxyaminobenzimidazole;
5(6)-(but-3-en-1-ylsulfinyl)-2-carbomethoxyaminobenzimidazole;
5(6)-(3-phenyl-prop-2-en-1-yloxy)-2-carbomethoxyaminobenzimidazole;
5(6)-phenylthioethoxy-2-carbomethoxyaminobenzimidazole;
5(6)-phenpropylthio-2-carbomethoxyaminobenzimidazole;
5(6)-phenpropylsulfinyl-2-carbomethoxyaminobenzimidazole;
5(6)-phenethoxy-2-carbomethoxyaminobenzimidazole;
5(6)-phenpropoxy-2-carbomethoxyaminobenzimidazole;
5(6)-(prop-2-en-1-yloxy)-2-carbomethoxyaminobenzimidazole;
5(6)-ethylsulfinylethylthio-2-carbomethoxyaminobenzimidazole;
5(6)-methylthioethylsulfinyl-2-carbomethoxyaminobenzimidazole and 5(6)-methylsulfinylethylthio-2-carbomethoxyaminobenzimidazole;
5(6)-ethylsulfinylethylsulfinyl-2-carbomethoxyaminobenzimidazole;
5(6)-methylsulfonylethoxy-2-carbomethoxyaminobenzimidazole;
5(6)-ethylthioethoxy-2-carbomethoxyaminobenzimidazole;
5(6)-ethylsulfinylethoxy-2-carbomethoxyaminobenzimidazole;
5(6)-(p-chlorophenylthiomethylsulfinyl)-2-carbomethoxyaminobenzimidazole; and 5(6)-(p-chlorophenylsulfinylmethylthio)-2-carbomethoxyaminobenzimidazole;
5(6)-phenylthioethylthio-2-carbomethoxyaminobenzimidazole;
5(6)-phenylsulfinylethylthio-2-carbomethoxyaminobenzimidazole;
5(6)-phenoxypropylthio-2-carbomethoxyaminobenzimidazole;
5(6)-phenoxypropylsulfinyl-2-carbomethoxyaminobenzimidazole;
5(6)-benzyloxyethylthio-2-carbomethoxyaminobenzimidazole;
5(6)-benzyloxyethylsulfinyl-2-carbomethoxyaminobenzimidazole;
5(6)-(t-butoxyethylthio)-2-carbomethoxyaminobenzimidazole;
5(6)-(t-butoxyethylsulfinyl)-2-carbomethoxyaminobenzimidazole;
5(6)-phenoxybutylthio-2-carbomethoxyaminobenzimidazole;
5(6)-(2,2-dimethoxyethylsulfinyl)-2-carbomethoxyaminobenzimidazole;
5(6)-(3-methoxypropylsulfinyl)-2-carbomethoxyaminobenzimidazole;
5(6)-benzyloxyethoxy-2-carbomethoxyaminobenzimidazole;
5(6)-phenoxypropoxy-2-carbomethoxyaminobenzimidazole;
5(6)-phenoxybutoxy-2-carbomethoxyaminobenzimidazole;
5(6)-(p-chlorophenoxyethoxy)-2-carbomethoxyaminobenzimidazole;
5(6)-(p-methoxyphenoxyethoxy)-2-carbomethoxyaminobenzimidazole;
5(6)-(p-methylphenoxyethoxy)-2-carbomethoxyaminobenzimidazole;
5(6)-[(2-methoxy)ethoxy-ethoxy]-2-carbomethoxyaminobenzimidazole;
5(6)-phenoxymethoxy-2-carbomethoxyaminobenzimidazole;
5(6)-benzyloxymethoxy-2-carbomethoxyaminobenzimidazole;
5(6)-phenylthiomethoxy-2-carbomethoxyaminobenzimidazole;
5(6)-phenylsulfinylmethoxy-2-carbomethoxyaminobenzimidazole;
5(6)-phenylsulfinylethoxy-2-carbomethoxyaminobenzimidazole;
5(6)-(p-methylbenzyloxyethoxy)-2-carbomethoxyaminobenzimidazole;
5(6)-(p-chlorobenzyloxyethoxy)-2-carbomethoxyaminobenzimidazole;
5(6)-(p-methoxybenzyloxyethoxy)-2-carbomethoxyaminobenzimidazole;
5(6)-phenoxymethylthio-2-carbomethoxyaminobenzimidazole;
5(6)-benzyloxymethylthio-2-carbomethoxyaminobenzimidazole;
5(6)-phenylthiomethylthio-2-carbomethoxyaminobenzimidazole;
5(6)-phenylsulfonylethoxy-2-carbomethoxyaminobenzimidazole;
5(6)-benzyloxyethylthio-2-carbomethoxyaminobenzimidazole;
5(6)-phenoxymethylsulfinyl-2-carbomethoxyaminobenzimidazole;
5(6)-benzyloxymethylsulfinyl-2-carbomethoxyaminobenzimidazole;
5(6)-phenylthiomethylsulfinyl-2-carbomethoxyaminobenzimidazole;
5(6)-phenylsulfinylmethylsulfinyl-2-carbomethoxyaminobenzimidazole;
5(6)-(4-chlorobutylsulfinyl)-2-carbomethoxyaminobenzimidazole;

5(6)-(diphenylmethoxyethylsulfinyl)-2-carbomethoxyaminobenzimidazole;

5(6)-[2-(4-methylthiophenoxy)ethoxy]-2-carbomethoxyaminobenzimidazole;

5(6)-[2-(4-methylsulfinylphenoxy)ethoxy]-2-carbomethoxyaminobenzimidazole;

5(6)-[2-(4-methylsulfonylphenoxy)ethoxy]-2-carbomethoxyaminobenzimidazole;

5(6)-[2-(4-methylthiobenzyloxy)ethoxy]-2-carbomethoxyaminobenzimidazole;

5(6)-[2-(4-methylsulfinylbenzyloxy)ethoxy]-2-carbomethoxyaminobenzimidazole;

5(6)-[2-(4-methylsulfonylbenzyloxy)ethoxy]-2-carbomethoxyaminobenzimidazole;

1-(n-butylcarbamoyl)-5(6)-(3-chloropropylsulfinyl)-2-carbomethoxyaminobenzimidazole;

1-(n-butylcarbamoyl)-5(6)-[2-(benzyloxy)ethoxy]-2-carbomethoxyaminobenzimidazole;

1-(n-butylcarbamoyl)-5(6)-(but-3-en-1-ylthio)-2-carbomethoxyaminobenzimidazole; and 1-(n-butylcarbamoyl)-5(6)-([2-(p-chlorophenoxy)ethoxy]-2-carbomethoxyaminobenzimidazole;

and the corresponding 2-carbethoxyamino, 2-carbopropoxyamino and 2-carbobutoxyamino compounds.

Of these compounds, 5(6)-benzyloxyethoxy-2-carbomethoxyaminobenzimidazole, 5(6)-(3-chloroprop-2-3n-1-yl-thio)-2-carbomethoxyaminobenzimidazole, 5(6)-(but-3-en-1-ylthio)-2-carbomethoxyaminobenzimidazole, 5(6)-(p-methylphenoxyethoxy-2-carbomethoxyaminobenzimidazole, 5(6)-(p-chlorophenoxyethoxy)-2-carbomethoxyaminobenzimidazole, 5(6)-(p-methoxyphenoxyethoxy)-2-carbomethoxyaminobenzimidazole, 5(6)-(3-chloroprop-1-ylsulfinyl)-2-carbomethoxyaminobenzimidazole, particularly 5(6)-(p-chlorophenoxyethoxy)-2-carbomethoxyaminobenzimidazole, 5(6)-benzyloxyethoxy-2-carbomethoxyaminobenzimidazole, 5(6)-(3-chloroprop-1-ylsulfinyl)-2-carbomethoxyaminobenzimidazole and 5(6)-(but-3-en-1-ylthio)-2-carbomethoxyaminobenzimidazole are presently preferred because they have shown substantial activity against the helminths specifically referred to above. Of particular interest are the compounds of the formula:

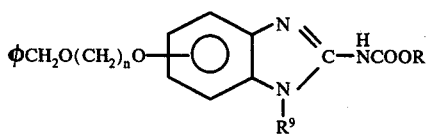
(II)

where R and n are as defined above, particularly where R is methyl and n is 2, and the phenyl ring in the $R^1$ moiety is optionally substituted with one or more halo, alkyl, alkoxy, alkylthio, alkylsulfinyl or alkylsulfonyl (as defined above) substituents, $R^9$ is hydrogen or —C(O)NHR$^8$; and $R^8$ is aryl, aralkyl, or lower alkyl having 1 to 12 carbon atoms and optionally substituted with a —COOR group where R is as defined above. Exemplary compounds within the class of compounds of Formula II are 5(6)-benzyloxyethoxy-2-carbomethoxyaminobenzimidazole, 5(6)-(4-chlorobenzyloxyethoxy)-2-carbomethoxyaminobenzimidazole, 5(6)-(4-bromobenzyloxyethoxy)-2-carbomethoxyaminobenzimidazole, 5(6)-(4-methylbenzyloxyethoxy)-2-carbomethoxyaminobenzimidazole, 5(6)-(4-methoxybenzyloxyethoxy)-2-carbomethoxyaminobenzimidazole, 5(6)-(2,4-dichlorobenzyloxyethoxy)-2-carbomethoxyaminobenzimidazole, 5(6)-(3,4-dichlorobenzyloxyethoxy)-2-carbomethoxyaminobenzimidazole, 5(6)-(4-methylthiobenzyloxyethoxy)-2-carbomethoxyaminobenzimidazole, 5(6)-(4-methylsulfinylbenzyloxyethoxy)-2-carbomethoxyaminobenzimidazole, 5(6)-(4-methylsulfonylbenzyloxyethoxy)-2-carbomethoxyaminobenzimidazole, 5(6)-(4-chloro-3-methylbenzyloxyethoxy)-2-carbomethoxyaminobenzimidazole, and 5(6)-(2,4,6-trichlorobenzyloxyethoxy)-2-carbomethoxyaminobenzimidazole.

Also of particular interest are the compounds of the formula:

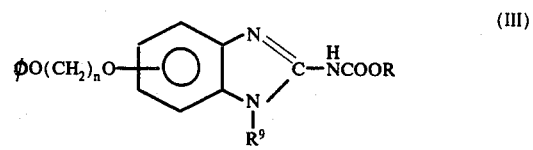
(III)

where R and n are as defined above, particularly where R is methyl and n is 2, and the phenyl ring in the $R^1$ moiety is substituted with one or more halo, alkyl, alkoxy, alkylthio, alkylsulfinyl or alkylsulfonyl (as defined above) substituents, $R^9$ is hydrogen or —C(O)NHR$^8$; and $R^8$ is aryl, aralkyl, or lower alkyl having 1 to 12 carbon atoms and optionally substituted with a —COOR group where R is as defined above. Exemplary compounds within the class of Formula III compounds are 5(6)-(4-chlorophenoxyethoxy)-2-carbomethoxyaminobenzimidazole, 5(6)-(4-bromophenoxyethoxy)-2-carbomethoxyaminobenzimidazole, 5(6)-(4-methylphenoxyethoxy)-2-carbomethoxyaminobenzimidazole, 5(6)-(4-methoxyphenoxyethoxy)-2-carbomethoxyaminobenzimidazole, 5(6)-(2,4-dichlorophenoxyethoxy)-2-carbomethoxyaminobenzimidazole, 5(6)-(3,4-dichlorophenoxyethoxy)-2-carbomethoxyaminobenzimidazole, 5(6)-(4-methylthiophenoxyethoxy)-2-carbomethoxyaminobenzimidazole, 5(6)-(4-methylsulfinylphenoxyethoxy)-2-carbomethoxyaminobenzimidazole, 5(6)-(4-methylsulfonylphenoxyethoxy)-2-carbomethoxyaminobenzimidazole, 5(6)-(4-chloro-3-methylphenoxyethoxy)-2-carbomethoxyaminobenzimidazole, and 5(6)-(2,4,6-trichlorophenoxyethoxy)-2-carbomethoxyaminobenzimidazole.

The compounds of the present invention, and the nontoxic salts thereof formed with pharmaceutically acceptable inorganic or organic acids, possess broad spectrum activity against parasites of mammals, including both mature and immature parasitic forms, as represented for example, by the genera Trichostronglylus, Haemonchus, Ostertagia, Cooperia, Nematodirus, and Stronglyoides, and specifically, for example against *Nematospiroides dubius, Hymenolepis Nana, Syphacia obvelata,* and/or *Aspiculuris tetraptera.* In particular, these compounds are found to exhibit high activity against various helminthic infections of the intestinal tract of economically important animals, coupled with low systemic toxicity to the host animal.

The compounds of the present invention are also useful as antifungal agents, particularly as systemic fungicides for controlling fungal diseases of plants of economic importance.

In addition to the stated anthelmintic and antifungal properties, certain compounds of the present invention are also useful as intermediates in the preparation of further compounds of this invention. For example, the 5(6)-substitutedthio compounds can be prepared and then utilized as starting materials for the preparation of the corresponding 5(6)-substitutedsulfinyl compounds.

Where the compound has a basic moiety, the term non-toxic salts as used herein refers to those pharmaceutically acceptable salts of the compounds of this invention which do not adversely affect the antifungal or anthelmintic properties of the basic compounds, such as those salts conventionally used in the art. Such non-toxic salts include, for example, salts of inorganic acids such as, for example, sulfuric, sulfonic, sulfamic, nitric, phosphoric, hydrochloric acids and the like, and salts of organic acids such as, for example, acetic, citric, lactic, palmitic, tartaric, succinic, maleic, benzoic acids and the like. Where the compound has an acidic moiety, the non-toxic salts include cation salts, such as, for example, the salts of sodium, potassium, ammonium, and the like.

The amount of the compound to be administered will depend upon the actual compound utilized, and upon the weight of the animal being treated. In general, however, the daily dosage level will usually be between about 5 mg/kg or less and 100 mg/kg of body weight of the animal being treated. The active ingredient is adapted to be administered to the animal by mixing it with the diet of the animal, as with a feed mix, or formulating it with a non-toxic carrier to give anthelmintic compositions. The carrier may be an orally ingestible container for the active ingredient such as, for example, a gelatin capsule, or it may be an excipient of the kind normally used in medicaments of this character, including maize starch, terra alba, lactose, sucrose, calcium phosphate, gelatin, stearic acid, agar, pectin or the like. Examples of suitable liquid carriers are peanut oil, sesame oil and water.

A wide variety of pharmaceutical forms can be employed in those cases wherein the medicament is not admixed with the feed. Thus, if a solid carrier is used, the compound can be administered in tablet or capsule form. If a liquid carrier is used, the medicament may be in the form of a soft gelatin capsule or in a liquid suspension.

The compounds of this invention can be prepared according to the procedures set forth in aforementioned applications Ser. Nos. 319,299 and 417,963, the entire disclosures of which (particularly those portions thereof relating to the methods of chemical preparations) are incorporated herein by reference.

DESCRIPTION OF SPECIFIC EMBODIMENTS

The following specific description is given to enable those skilled in this art to more clearly understand and practice the present invention. It should not be considered as a limitation upon the scope of the invention but merely as being illustrative and representative thereof.

Unless otherwise indicated, all temperatures are in degrees centigrade and all percentages are by weight.

PREPARATION 1

175 G. of S-methyl isothiouronium sulfate in one liter of water is cooled to 0° C and 162.5 g. of methylchloroformate added, followed by the addition of a solution of 250 g. potassium hydroxide in 750 ml. water at 0° to 5° C. The crude product is extracted into benzene, the benzene dried and evaporated, and the residue recrystallized from methanol. 1,3-bis(methoxycarbonyl)-S-methyl isothiourea is thus obtained.

In a similar manner, substituting ethylchloroformate, propylchloroformate and butylchloroformate for the methylchloroformate, 1,3-bis(ethoxycarbonyl)-S-methyl isothiourea, 1,3-bis(propoxycarbonyl)-S-methyl isothiourea, and 1,3-bis(butoxycarbonyl)-S-methyl isothiourea are, respectively, prepared.

EXAMPLE 1

6 G. of 2-nitro-4-thiocyanathoaniline in 30 ml. of dimethylformamide is treated under nitrogen with 1.2 g. of sodium borohydride at 20° to 30°. After 1½ hours 15 ml. of acetone is added, followed 2 hours later by 10 g. of 3-chloropropylbromide. The mixture is left at 20°–25° for 16 hours, then diluted with water. The oily product is extracted into chloroform and passed through a silica column. 2-Nitro-4-(3-chloropropylthio)aniline is isolated by evaporation of the solvent.

6 G. of 2-nitro-4-(3-chloropropylthio)aniline is treated in 120 ml. of methanol and 120 ml. of water with 30 g. of sodium hydrosulfite ($Na_2S_2O_4$) on the steam bath for about 5 minutes. The reaction mixture is concentrated under vacuum and extracted well with chloroform. Evaporation of the dried extract affords 1,2-diamino-4-(3-chloropropylthio)benzene.

4 G. of 1,2-diamino-4-(3-chloropropylthio)benzene and 4.2 g. of 1,3-bis(methoxycarbonyl)-S-methyl isothiourea are heated in a mixture of 40 ml. of ethanol, 40 ml. of water and 1.5 ml. of acetic acid for 4 hours at reflux. The mixture is cooled and 5(6)-(3-chloropropylthio)-2-carbomethoxyaminobenzimidazole filtered off. Recrystallization may be effected from methanol chloroform (m.p. 201.5°–202.5°).

1.5 G. of 5(6)-(3-chloropropylthio)-2-carbomethoxyaminobenzimidazole is dissolved in 100 ml. of chloroform and 10 ml. of acetic acid at −20°. A solution of 1.05 g. of m-chloroperbenzoic acid in 30 ml. of chloroform is added and the mixture allowed to warm slowly to 20°–25°. After 3 hours at 20°–25° the mixture is concentrated under vacuum and the residue treated with sodium bicarbonate solution. The crude product is filtered off and recrystallized from methanol to afford 5(6)-(3-chloropropylsulfinyl)-2-carbomethoxyaminobenzimidazole (m.p. 206° dec.).

EXAMPLES 2 and 3

The procedure of Example 1 is repeated substituting 1,2,3-trichloropropene for the 3-chloropropyl bromide to afford 5(6)-(2,3-dichloroprop-2-en-1-ylthio)-2-carbomethoxyaminobenzimidazole (m.p. 182° dec.) and 5(6)-(2,3-dichloroprop-2-en-1-ylsulfinyl)-2-carbomethoxyaminobenzimidazole (m.p. ~270° dec.).

EXAMPLES 4 and 5

The procedure of Example 1 is repeated substituting 4-bromobut-1-ene for the 3-chloropropyl bromide to afford 5(6)-(but-3-en-1-ylthio)-2-carbomethoxyaminobenzimidazole (m.p. ~200° dec.) and 5(6)-(but-3-en-1-ylsulfinyl)-2-carbomethoxyaminobenzimidazole (m.p. ~230° dec.).

EXAMPLES 6 and 7

The procedure of Example 1 is repeated substituting 2-(t-butoxy)ethyl bromide for the 3-chloropropyl bromide to afford 5(6)-(t-butoxyethylthio)-2-carbomethoxyaminobenzimidazole (m.p. 175°–179°) and 5(6)-(t-butoxyethylsulfinyl)-2-carbomethoxyaminobenzimidazole (m.p. 156° dec.).

EXAMPLES 8 and 9

The procedure of Example 1 is repeated substituting 2-benzyloxyethyl-methane sulfonate (prepared in pyridine from 2-benzyloxyethanol and methanesulfonyl chloride) for the 3-chloropropyl bromide to afford 5(6)-benzyloxyethylthio-2-carbomethoxyaminobenzimidazole (m.p. 182° dec.). and 5(6)-benzyloxyethylsulfinyl)-2-carbomethoxyaminobenzimidazole (m.p. 190° dec.).

EXAMPLES 10 – 14

The procedure of Example 1 is repeated substituting 2,2-bismethoxyethyl bromide, 3-bromopropanol, 1,1,2-trichloroethane, 1-bromo-3-methoxypropane, and 1-bromo-4-phenoxybutane for the 3-chloropropyl bromide to afford, respectively, 5(6)-(2,2-dimethoxyethylsulfinyl)-2-carbomethoxyaminobenzimidazole (m.p. ~152° dec.), 5(6)-(2-hydroxypropylsulfinyl)-2-carbomethoxyaminobenzimidazole (m.p. ~203° dec.), 5(6)-(2,2-dichloroethylsulfinyl)-2-carbomethoxyaminobenzimidazole (m.p. 210° dec.), 5(6)-(3-methoxypropylsulfinyl)-2-carbomethoxyaminobenzimidazole (m.p. 170° dec.), and 5(6)-phenoxybutylthio-2-carbomethoxyaminobenzimidazole (m.p. 189°–191° dec.).

EXAMPLE 15

A solution of 7.5 g. of 2-benzyloxyethanol in 30 ml. of dimethylformamide is treated with 1.2 g. of sodium hydride. When the mixture is homogeneous, 3.5 g. of 2-amino-4-chloro-1-nitrobenzene is added and the mixture heated at 110°–120° for 4 hours. The mixture is cooled, diluted with water and extracted with benzene. The crude product is treated with charcoal and isolated by precipitation with cyclohexane to afford 2-amino-1-nitro-4-(2-benzyloxyethoxy)benzene.

1.6 G. of 2-amino-4-(2-benzyloxyethoxy)-1-nitrobenzene is treated in 100 ml. of methanol and 50 ml. of water with 10 g. of sodium hydrosulfite ($Na_2S_2O_4$) on the steam bath for 15 minutes. The reaction mixture is concentrated under vacuum and extracted with chloroform. Evaporationn of the extract affords 1,2-diamino-4-(2-benzyloxyethoxy)benzene.

1.4 G. of 1,2-diamino-4-(2-benzyloxyethoxy)benzene and 1.4 g. of 1,3-bis(methoxycarbonyl)-S-methyl isothiourea is treated in 20 ml. of ethanol and 20 ml. of water with 0.5 ml. of acetic acid. After refluxing for 5 hours the mixture is cooled and filtered. Recrystallization of the product from methanol-chloroform affords 5(6)-(2-benzyloxyethoxy)-2-carbomethoxyaminobenzimidazole (m.p. ~191° dec.).

EXAMPLE 16

The procedure of Example 15 is repeated substituting 2-methylthioethanol for the 2-benzyloxyethoxy to afford 5(6)-(2-methylthioethoxy)-2-carbomethoxyaminobenzimidazole. This product is treated in accordance with the last paragraph of Example 1 substituting peracetic acid (2 moles) for the m-chloroperbenzoic acid to afford 5(6)-(2-methylsulfonylethoxy)-2-carbomethoxyaminobenzimidazole (m.p. 225°–226° dec.).

EXAMPLES 17 and 18

4.7 G. of 2-nitro-4-thiocyanatoacetanilide is dissolved in 30 ml. of dimethylformamide under nitrogen. 0.8 G. of sodium borohydride is added at 20°–30°. After 1 hour 10 ml. of acetone is added and then after a further 2 hours, 2.7 g. of 1,3-dichloropropene is added. The mixture is left for 24 hours at 20°–25°, then drowned into water. 2-Nitro-4-(3 -chloro-prop-2-en-1-ylthio)acetanilide is filtered off and purified by passage, in chloroform solution, through a column of silica.

4.3 G. of the product of the preceding paragraph is treated at 20°–25° with 50 ml. of ethanol containing 10 ml. of 5N aqueous sodium hydroxide. After 1 hour 10 ml. of water is added followed by 20 g. of sodium hydrosulfite. The mixture is warmed for about 5 minutes until the orange color is discharged and then stripped near vacuum and diluted with water. 1,2-diamino-4-(3-chloro-prop-2-en-1-yl-thio)benzene is isolated by chloroform extraction.

2.9 G. of the product of the preceding paragraph is treated with 3.3 g. of 1,3-bis(methoxycarbonyl)-S-methyl isothiourea and 1.5 ml. of acetic acid in 30 ml. of ethanol and 30 ml. of water on the steam bath for 4 hours. The mixture is cooled and filtered. Recrystallization from methanol affords 5(6)-(3-chloro-prop-2-en-1-ylthio)-2-carbomethoxyaminobenzimidazole (m.p. ~202° dec.).

The product of the preceding paragraph is treated in accordance with the procedure of the last paragraph of Example 1 to afford 5(6)-(3-chloro-prop-2-en-1-ylsulfinyl)-2-carbomethoxyaminobenzimidazole (m.p. 240° dec.).

EXAMPLES 19 and 20

The procedure of Examples 17 and 18 is repeated substituting 3-phenoxypropyl bromide for the 1,3-dichloropropane to afford 5(6)-(3-phenoxypropylthio)-2-carbomethoxyaminobenzimidazole (m.p. 196° dec.) and 5(6)-(3-phenoxypropylsulfinyl)-2-carbomethoxyaminobenzimidazole (m.p. 189° dec.).

EXAMPLES 21 and 22

The procedure of Examples 17 and 18 is repeated substituting 2,3-dichloropropene for the 1,3-dichloropropene to afford 5(6)-(2-chloro-prop-2-en-1-ylthio)-2-carbomethoxyaminobenzimidazole (m.p. ~211° dec.) and 5(6)-(2-chloro-prop-2-en-1-ylsulfinyl)-2-carbomethoxyaminobenzimidazole (m.p. ~188° dec.).

EXAMPLE 23

The procedure of Example 17 is repeated except 2-(phenylthio)ethyl chloride is substituted for the 1,3-dichloropropene to afford 5(6)-[2-(phenylthio)ethylthio]-2-carbomethoxyaminobenzimidazole (m.p. 210°–212°).

EXAMPLE 24

The procedure of the first paragraph of Example 17 is repeated substituting 2-(phenylsulfinyl)ethyl chloride [prepared by treating 2-(phenylthio)ethyl chloride with peracetic acid] for the 1,3-dichloropropene to afford 1-acetamido-2-nitro-4-[2-(phenylsulfinyl)ethylthio]benzene.

5 G. of the product of the preceding paragraph is treated at 20°–25° with 50 ml. of methanol containing 10 ml. of 5N aqueous sodium hydroxide. After 1 hour 250 ml. of methanol and 50 ml. of water with 3 g. of ferrous sulfate and 25 g. of iron powder (activated with 1 ml. of hydrochloric acid) are added and held at reflux for 18 hours. After the iron residue is filtered off, the filtrate is concentrated under vacuum to afford 1,2-diamino-4-[2-(phenylsulfinyl)ethylthio]benzene.

The product of the preceding paragraph is treated in accordance with the third paragraph of Example 17 to afford 5(6)-[2-(phenylsulfinyl)ethylthio]-2-carbomethoxyaminobenzimidazole (m.p. 186°–188°).

EXAMPLE 25

The procedure of the first paragraph of Example 17 is repeated substituting 2-(ethylsulfinyl)ethyl bromide [prepared by treating 2-(ethylthio)ethyl bromide with peracetic acid] for the 1,3-dichloropropene to afford 1-acetamido-2-nitro-4-[2-(ethylsulfinyl)ethylthio]benzene. This product is treated in accordance with the second and third paragraphs of Example 24 to afford 5(6)-[2-(ethylsulfinyl)ethylthio]-2-carbomethoxyaminobenzimidazole (m.p. ~190° dec.).

EXAMPLE 26

A mixture of 4.1 g. of 2-nitro-4-hydroxy-acetanilide, 4.7 g. of 3-phenoxypropylbromide and 3.1 g. of potassium carbonate in 100 ml. of acetone is treated under reflux for 16 hours. The mixture is diluted with water and the 2-nitro-4-(2-phenoxypropoxy)acetanilide is filtered off.

The product of the preceding paragraph is treated in accordance with the second and third paragraphs of Example 17 to afford 5(6)-(3-phenoxypropoxy)-2-carbomethoxyaminobenzimidazole (m.p. ~220° dec.).

EXAMPLE 27–29

The procedure of Example 26 is repeated substituting 2-(ethylthio)ethyl bromide, allyl bromide and 3-phenyl-1-bromopropane for the 3-phenoxypropyl bromide to afford, respectively, 5(6)-[2-(ethylthio)ethoxy]-2-carbomethoxyaminobenzimidazole (m.p. 208° dec.), 5(6)-(prop-2-en-1-yloxy)-2-carbomethoxyaminobenzimidazole (m.p. 217° dec.) and 5(6)-(3-phenylpropoxy)-2-carbomethoxyaminobenzimidazole (m.p. 204° dec.).

EXAMPLE 30

The 5(6)-[2-(ethylthio)ethoxy]-2-carbomethoxyaminobenzimidazole of Example 27 is treated in accordance with the last paragraph of Example 1 to afford 5(6)-[2-(ethylsulfinyl)ethoxy]-2-carbomethoxyaminobenzimidazole (m.p. 212° dec.).

EXAMPLES 31 and 32

3.45 G. of 2-amino-4-chloro-1-nitrobenzene and 5.3 g. of sodium sulfide monohydrate in 30 ml. of dimethylformamide is heated at about 100° for 1 hour under nitrogen, cooled and 4.5 g. of 3-phenylpropyl bromide added, held at 20°–25° for 4 hours, then diluted with water. The product is filtered off and recrystallized from methanol to afford 2-amino-4-(3-phenylpropylthio)-1-nitrobenzene.

3.5 G. of the product of the preceding paragraph and 3.5 g. of iron powder in 100 ml. of toluene, 3.5 ml. of water and 0.2 ml. of concentrated hydrochloric acid is refluxed for 2 hours, cooled, filtered and the filtrate evaporated to afford 1,2-diamino-4-(3-phenylpropylthio)benzene. This product is treated in accordance with the third and fourth paragraphs of Example 1 to afford 5(6)-(3-phenylpropylthio)-2-carbomethoxyaminobenzimidazole (m.p. 181°–185°) and 5(6)-(3-phenylpropylsulfinyl)-2-carbomethoxyaminobenzimidazole (m.p. ~207° dec.).

EXAMPLES 33 and 34

The procedure of the first paragraph of Examples 31 and 32 and the procedure of the second, third and fourth paragraphs of Example 1 are repeated substituting cinnamyl bromide for the 3-phenylpropyl bromide to afford 5(6)-(3-phenylprop-2-en-1-ylthio)-2-carbomethoxyaminobenzimidazole (m.p. 270° dec.). and 5(6)-(3-phenylprop-2-en-1-ylsulfinyl)-2-carbomethoxyaminobenzimidazole (m.p. 223° dec.).

EXAMPLE 35

A mixture of 4.6 g. of 2-nitro-4-acetoxy-acetanilide and 5.6 g. of potassium carbonate in 150 ml. of methanol is refluxed for 5 minutes and then 12 g. of 2-phenylthioethylmethanesulfonate (prepared from 2-phenylthioethanol in pyridine with methanesulfonyl chloride and isolated from acidified water by ether extraction) is added. The mixture is refluxed for 16 hours then 10 ml. of water is added and the solute concentrated for about 1 hour. Water is added and the product filtered off and washed with water and hexane to afford 2-nitro-4-[2-(phenylthio)ethoxy]aniline.

2.8 G. of the product of the preceding paragraph is treated in 125 ml. of methanol and 25 ml. of water with 15 g. of sodium hydrosulfite on the steam bath for about 10 minutes. The mixture is concentrated under vacuum, diluted with water and extracted into chloroform. Evaporation of the dried extract affords 1,2-diamino-4-[2-(phenylthio)ethoxy]benzene.

1.8 G. of the product of the preceding paragraph is treated with 2 g. of 1,3-bis(methoxycarbonyl)-S-methyl isothiourea and 1 ml. of acetic acid in 25 ml. of ethanol and 25 ml. of water on the steam bath for 6 hours. The mixture is cooled and the product filtered off. Recrystallization from methanol-chloroform affords 5(6)-[2-(phenylthio)ethoxy[-2-carbomethoxyaminobezimidazole (m.p. 210° dec.).

EXAMPLE 36

The procedure of Example 35 is repeated substituting 2-phenylethyl bromide for the 2-phenylthioethyl methanesulfonate to afford 5(6)-(2-phenylethoxy)-2-carbomethoxyaminobenzimidazole (m.p. 222° dec.).

EXAMPLES 37–39

2 G. of 4-(2-bromoethoxy)-2-nitroacetanilide in 40 ml. of acetone containing 0.95 g. of potassium carbonate is treated with 0.75 g. of p-cresol. This mixture is stirred overnight at reflux, then cooled, filtered and the solvent removed by vacuum distillation to give 4-[2-(p-methylphenoxy)ethoxy]-2-nitroacetanilide as a yellow gum. This may be used without purification or can be recrystallized from methanol.

2 G. of 4-[2-(p-methylphenoxy)ethoxy]-2-nitroacetanilide in 10 ml. of methanol is treated with 4 ml. of 5H NaOH solution. The mixture is heated for 20 minutes, then cooled and diluted with water. The precipitated 4-[2-(p-methylphenoxy)ethoxy]-2-nitroaniline is collected, washed well with water and dried.

1.6 G. of 4-[2-(p-methylphenoxy)ethoxy]-2-nitroaniline in 20 ml. of methanol containing 0.5 g. of 5% palladized charcoal is hydrogenated at 1 atmosphere pressure until the theoretical uptake of hydrogen has occurred. The catalyst is removed by filtration and the filtrate evaporated. The residual gum is treated with 1.8 g. of 1,3-bis-(methoxycarbonyl)-S-methyl isothiourea and 0.4 ml. of acetic acid in a boiling mixture of 10 ml. of ethanol and 10 ml. of water. After 3 hours the mixture is cooled, filtered and 5(6)-[2-(p-methylphenoxy)ethoxy]-2-carbomethoxyaminobenzimidazole is recrystallized from a mixture of methanol and chloroform (m.p. 210°–212° dec.).

In a similar manner, substituting p-methoxyphenol and p-chlorophenol for the p-cresol, 5(6)-[2-(p-methoxyphenoxy)ethoxy]-2-carbomethoxyaminobenzimidazole (m.p. 208°–211° dec.), and 5(6)-[2-(p-chlorophenoxy)ethoxy]-2-carbomethoxyaminobenzimidazole (m.p. 205°–207° dec.) are prepared.

EXAMPLE 40

The procedure of the first paragraph of Example 26 is repeated substituting 4-phenxoybutyl bromide for the 3-phenoxypropyl bromide to afford 2-nitro-4-(4-phenoxybutoxy)acetanilide. After treatment at 20°–25° with methanolic-5N aqueous sodium hydroxide, 1.2 g. of the resultant 2-nitro-4-(4-phenoxybutoxy)aniline in a mixture of 20 ml. of methanol and 0.3 g. of 5% palladized charcoal is hydrogenated under ambient conditions. When the theoretical amount of hydrogen has been taken up, the mixture is filtered and the filtrate stripped to afford 1,2-diamino-4-(4-phenoxybutoxy)-benzene as a gum.

The procedure of the last paragraph of Example 15 is repeated to afford 5(6)-(4-phenoxybutoxy)-2-carbomethoxyaminobenzimidazole (m.p. 190°–193° dec.).

EXAMPLE 41

The procedure of Example 40 is repeated substituting cinnamyl bromide for the 4-phenoxybutyl bromide to afford 5(6)-(3-phenyl-prop-2-en-1-yloxy)-2-carbomethoxyaminobenzimidazole (m.p. 215°–218° dec.).

EXAMPLE 42

The procedure of the first paragraph of Example 15, the catalytic reduction of the first paragraph of Example 41, and the third paragraph of Example 15 are repeated substituting 2-(2-methoxyethoxy)ethanol for the 2-benzyloxyethanol to afford 5(6)-[2-(2'-methoxyethoxy)ethoxy]2-carbomethoxyaminobenzimidazole (m.p. 184°–185° dec.).

EXAMPLE 43

5.85 G. of 1-amino-2-nitro-4-thiocyanatobenzene in 20 ml. dimethylformamide is treated under nitrogen with 1.14 g. sodium borohydride at not greater than 30°. The mixture is stirred for one hour at 15°–20°, then treated with 12 g. of 1,3-dibromopropane at 20°–25°. After a further 3 hours, water is added and the crude product extracted with chloroform. The dried chloroform solution is passed through a column of silica gel to remove polar material. Pure 1-amino-2-nitro-4-(3-bromopropylthio)benzene is obtained from the eluate.

3.0 G. of 1-amino-2-nitro-4-(3-bromopropylthio)-benzene in 18 ml. concentrated hydrochloric acid is treated with a solution of 10 g. stannous chloride. The mixture is cooled to about −30°, the product is filtered off and washed with 10 ml. of 6N hydrochloric acid. The product is dissolved in 30 ml. of water and treated with potassium acetate to pH of 3–4, then added to 25 ml. of ethanol. 3 G. of 1,3-bis-methoxycarbonyl-S-methyl isothiourea is added and the reaction mixture is held at reflux for three hours. The mixture is cooled and 5(6)-(3-bromopropylthio)-2-carbomethoxyaminobenzimidazole isolated by filtration. Recrystallization may be effected from methanol-chloroform (m.p. 185° dec.).

0.7 G. of 5(6)-(3-bromopropylthio)-2-carbomethoxyaminobenzimidazole is dissolved in a mixture of 2 ml. acetic acid and 50 ml. chloroform. A solution of 0.42 g. m-chloroperbenzoic acid in 20 ml. chloroform is added at −20° to −15°. The mixture is allowed to warm slowly to 20° and left for 5 hours. The solvents are removed under vacuum and the residue treated with sodium bicarbonate solution. 5(6)-(3-bromopropylsulfinyl)-2-carbomethoxyaminobenzimidazole is filtered off, and may be recrystallized from isopropanol (m.p. 169° dec.).

EXAMPLE 44

5.85 G. of 1-amino-2-nitro-4-thiocyanatobenzene is treated in 20 ml. dimethylformamide under nitrogen at 20°–25° with 1.14 g. sodium borohydride. After 1 hour 10 ml. of methylthioethylchloride is added and the mixture stirred overnight, diluted with water and extracted with chloroform. The dried chloroform solution is passed through a silica gel column, then evaporated to dryness to afford 1-amino-2-nitro-4-methylthioethyl-thiobenzene.

2.5 G. of 1-amino-2-nitro-4-methylthioethylthiobenzene in 160 ml. methanol and 40 ml. water is treated at reflux for 5 hours with 1.25 g. ferrous sulfate and 5 g. iron powder (the latter added in 2 portions). The mixture is filtered, stripped and the residual 1,2-diamino-4-methylthioethylthiobenzene extracted into chloroform, washed, dried and isolated by evaporation of the solvent.

1.8 G. 1,2-diamino-4-methylthioethylthiobenzene and 1.9 g. 1,3-bis(methoxycarbonyl)-S-methyl isothiourea and 0.8 ml. acetic acid in 20 ml. ethanol plus 20 ml. water are refluxed for 5 hours, cooled and filtered. The product, 5(6)-methylthioethylthio-2-carbomethoxyaminobenzimidazole, is purified by recrystallization from methanol-chloroform.

The product of the preceding paragraph is treated in accordance with the last paragraph of Example 1 using peracetic acid instead of m-chloroperbenzoic to afford 5(6)-(2-methylthioethylsulfinyl)-2-carbomethoxyaminobenzimidazole, 5(6)-(2-methylsulfinylethylthio) or a mixture thereof (m.p. 172° dec.).

EXAMPLE 45

The procedure of Example 44 is repeated substituting ethylthioethyl chloride for the methylthioethyl chloride and using two equivalents of peracetic acid to afford 5(6)-[2-(ethylsulfinyl)ethylsulfinyl]-2-carbomethoxyaminobenzimidazole (m.p. 169° dec.).

EXAMPLE 46

The procedure of Example 17 is repeated substituting p-chlorophenylthiomethyl chloride for the 1,3-dichloropropene to afford 5(6)-(p-chlorophenylthiomethylsulfinyl)-2-carbomethoxyaminobenzimidazole, 5(6)-(p-chlorophenylsulfinylmethylthio)-2-carbomethoxyaminobenzimidazole, or a mixture thereof (m.p. ~174° dec.).

EXAMPLES 47 and 48

The product of Examples 35 is oxidized in accordance with the last paragraph of Example 1 with one equivalent of m-chloroperbenzoic acid to afford 5(6)-[2-(phenylsulfinyl)ethoxy]-2-carbomethoxyaminobenzimidazole (m.p. 230° dec.), and with two equivalents of m-chloroperbenzoic acid to afford 5(6)-[2-(phenylsulfonyl)ethoxy]-2-carbomethoxy-aminobenzimidazole.

EXAMPLES 49–52

The procedure of Example 26 is repeated substituting phenoxymethylchloride, benzyloxymethylchloride, phenylthiomethylchloride and phenylsulfinylmethylchloride for the 3-phenoxypropylbromide to afford, respectively, 5(6)-phenoxymethoxy-2-carbomethoxyaminobenzimidazole, 5(6)-benzyloxymethoxy-2-carbomethoxyaminobenzimidazole, 5(6)-phenylthiomethoxy-2-carbomethoxyaminobenzimidazole, and 5(6)-phenylsulfinylmethoxy-2-carbomethoxyaminobenzimidazole.

EXAMPLES 53–55

The procedure of Example 15 is repeated substituting 2-(p-methylbenzyloxy)ethanol, 2-(p-chlorobenzyloxy)ethanol, and 2-(p-methoxybenzyloxy)ethanol for the 2-benzyloxyethanol to afford, respectively, 5(6)-(p-methylbenzyloxyethoxy)-2-carbomethoxyaminobenzimidazole, 5(6)-(p-chlorobenzyloxyethoxy)-2-carbomethoxyaminobenzimidazole, and 5(6)-(p-methoxybenzyloxyethoxy)-2-carbomethoxyaminobenzimidazole.

EXAMPLES 56–59

The procedure of Example 1 is repeated substituting phenoxymethylchloride, benzyloxymethylchloride, phenylthiomethylchloride and diphenylmethoxyethylchloride for the 3-chloropropylbromide to afford, respectively, 5(6)-phenoxymethylthio-2-carbomethoxyaminobenzimidazole, 5(6)-benzyloxymethylthio-2-carbomethoxyaminobenzimidazole, 5(6)-phenylthiomethylthio-2-carbomethoxyaminobenzimidazole, and 5(6)-(diphenylmethoxyethylthio)-2-carbomethoxyaminobenzimidazole.

EXAMPLES 60–63

The products of Examples 56–59 are oxidized in accordance with the last paragraph of Example 1 to afford 5(6)-phenoxymethylsulfinyl-2-carbomethoxyaminobenzimidazole, 5(6)-benzyloxymethylsulfinyl-2-carbomethoxyaminobenzimidazole, 5(6)-phenylthiomethylsulfinyl-2-carbomethoxyaminobenzimidazole, and 5(6)-diphenylmethoxyethylsulfinyl-2-carbomethoxyaminobenzimidazole.

EXAMPLE 64

5(6)-Phenylthiomethylthio-2-carbomethoxyaminobenzimidazole of Example 58 is treated with two equivalents of m-chloroperbenzoic acid in accordance with the procedure of the last paragraph of Example 1 to afford 5(6)-phenylsulfinylmethylsulfinyl-2-carbomethoxyaminobenzimidazole.

EXAMPLE 65

The procedure of Example 1 is repeated substituting 4-chlorobutylbromide for the 3-chloropropylbromide to afford 5(6)-(4-chlorobutylsulfinyl)-2-carbomethoxyaminobenzimidazole.

EXAMPLES 66–68

The procedure of Example 37 is repeated substituting p-methylthiophenol for the p-cresol to afford 5(6)-[2-(p-methylthiophenoxy)ethoxy]-2-carbomethoxyaminobenzimidazole. This product is treated with one or two equivalents of m-chloroperbenzoic acid to afford, respectively, 5(6)-[2-(p-methylsulfinylphenoxy)ethoxy]-2-carbomethoxyaminobenzimidazole and 5(6)-[2-(p-methylsulfonylphenoxy)ethoxy]-2-carbomethoxyaminobenzimidazole.

EXAMPLES 69–71

The procedure of Example 15 is repeated substituting 2-(p-methylthiobenzyloxy)ethanol for the 2-benzyloxyethanol to afford 5(6)-[2-(p-methylthiobenzyloxy)ethoxy]-2-carbomethoxyaminobenzimidazole. This product is treated with one or two equivalents of m-chloroperbenzoic acid to afford, respectively, 5(6)-[2-(p-methylsulfinylbenzyloxy)ethoxy]-2-carbomethoxyaminobenzimidazole and 5(6)-[2-(p-methylsulfonylbenzyloxy)ethoxy]-2-carbomethoxyaminobenzimidazole.

EXAMPLES 72–75

The compounds of Examples 1–71 can be reacted with a substituted isocyanate of the formula OCNR$^8$ where R$^8$ is aryl (e.g., phenyl), aralkyl (e.g., benzyl) or lower alkyl having 1 to 12 carbon atoms optionally substituted with a —COOR group where R is a lower alkyl having 1 to 4 carbon atoms, such as, for example, n-butylisocyanate, in an inert organic solvent, for example, tetrahydrofuran at about 0° to about 40° C for about one-half hour to about 96 hours to afford the corresponding 1-substituted derivative thereof.

5(6)-(3-Chloropropylsulfinyl)-2-carbomethoxyaminobenzimidazole of Example 1, 5(6)-(benzyloxyethoxy)-2-carbomethoxyaminobenzimidazole of Example 15, 5(6)-(but-3-en-1-ylthio)-2-carbomethoxyaminobenzimidazole of Example 17, and 5(6)-(p-chlorophenoxyethoxy)-2-carbomethoxyaminobenzimidazole of Example 39, are treated with n-butylisocyanate at 20°–25° C for 24 hours, followed by conventional work-up, to afford, respectively, 1-(n-butylisocyanate)-5-(6)-(3-chloropropylsulfinyl)-2-carbomethoxyaminobenzimidazole, 1-(n-butylisocyanate)-5(6)-(benzyloxyethoxy)-2-carbomethoxyaminobenzimidazole, 1-(n-butylisocyanate)-5(6)-(but-3-en-1-ylthio)-2-carbomethoxyaminobenzimidazole, and 1-(n-butylsiocyanate)-5(6)-(p-chlorophenoxyethoxy)-2-carbomethoxyaminobenzimidazole.

By substituting 1,3-bis(ethoxycarbonyl)-S-methyl (ethoxycarbonyl)-S-methyl isothiourea, 1,3-bis(-propoxycarbonyl)-S-methyl isothiourea, or 1,3-bis(-butoxycarbonyl)-S-methyl isothiourea for the 1,3-bis(-methoxycarbonyl)-S- methyl isothiourea used in the Examples above, the corresponding 2-carbalkoxyamino-5(6)-substitutedbenzimidazole compounds can be prepared, where R is either ethyl, propyl or butyl.

In certain of the Examples above, specific reaction sequences have been extended, in a general sense, to the preparation of other similar and related compounds. It should be understood, however, that with respect to any compound which has been prepared by the extension of a specific reaction sequence, it may be necessary or desirable to utilize solvents, reaction media, recrystallization media, reaction times or temperatures, or amounts of materials, etc., other than the ones given in the specific reaction sequence upon which such extension is based. Additionally, the specific reaction sequence or manner in which particular compounds are to be prepared will depend, inter alia, upon the availability of the necessary starting materials, or the ease in which the desired starting materials can be prepared, and the reactivity thereof. These variations are deemed to be within the skill of those working in this art and will be apparent from a consideration of the particular reactants utilized and/or particular compound desired to be produced.

EXAMPLE 76

Four young Swiss-Webster male mice (16–20 g.) are artifically infected with 200 larvae of the species *Nematospiroides dubius* (roundworm) and *Hymenolepis nana* (tapeworm) and naturally injected with 15–40 larvae of *Syphacia obvelata* and *Aspiculuris tetraptera* (pinworms). The drug is administered in a commercial rat/mouse diet at the stated dose(s) from day 1 through day 18, the infection being introduced at day 0. The animals are sacrificed at day 18 and the parasites remaining in the entire small intestine, cecum and large bowel are counted and differentiated. The average number of each parasite remaining in each medicated group is compared to the average number remaining in the control. This comparison is expressed as percent reduction over the parasites in the control group. The data for illustrative compounds of this invention is tabulated in the Table below.

| 5(6)-$R^1$-2-carbomethoxyaminobenzimidazoles | | | | | | |
|---|---|---|---|---|---|---|
| $R^1$ | Ex. | dose,* ppm | Test species (% reduction) | | | |
| | | | Nd | Hn | So | At |
| 3-chloropropyl-sulfinyl | 1 | 125 | 100 | 0 | 100 | 100 |
| | | 62(3) | 87.3 | 0 | 100 | 100 |
| | | 31(2) | 59 | 0 | 100 | 100 |
| | | 16 | 0 | 0 | 76 | 0 |
| but-3-en-1-ylthio | 4 | 125 | 100 | 0 | 100 | 100 |
| | | 62(2) | 98.5 | 0 | 100 | 100 |
| | | 31 | 69 | 0 | 100 | 100 |
| 3-methoxypropylsulfinyl | 13 | 125 | 100 | 0 | 100 | 100 |
| | | 62 | 80 | 0 | 100 | 100 |
| 2-(benzyloxy)-ethoxy | 15 | 125 | 95 | 100 | 100 | 100 |
| | | 62(2) | 80.5 | 100 | 100 | 100 |
| | | 31 | 0 | 73 | 100 | 100 |
| 3-chloroprop-2-en-1-ylthio | 17 | 125 | 100 | 0 | 100 | 100 |
| | | 62 | 84 | 0 | 100 | 100 |
| prop-2-en-1-yl-oxy | 28 | 125 | 89 | 85 | 100 | 100 |
| | | 62 | 70 | 0 | 100 | 100 |
| p-methylphenoxyethoxy | 37 | 62 | 83 | 69 | 100 | 100 |
| | | 31 | 0 | 0 | 100 | 100 |
| p-methoxyphenoxyethoxy | 38 | 62 | 50 | 69 | 100 | 100 |
| | | 31 | 0 | 0 | 100 | 100 |
| p-chlorophen-oxyethoxy | 39 | 62 | 80 | 62 | 100 | 100 |
| | 31 | 61 | 50 | 100 | 100 | |

Nd = *Nematospiroides dubius*
Hn = *Hymenolepis nana*
So = *Syphacia obvelata*
At = *Aspiculuris tetraptera*
*The number in parentheses refers to the number of runs from which percent reductions are calculated and averaged to give the data set forth for that particular dose in this Table.

While the present invention has been described with reference to specific embodiments thereof, it should be understood by those skilled in this art that various changes may be made and equivalents may be substituted without departing from the true spirit and scope of the invention. In addition, many modifications may be made to adapt a particular situation, material or composition of matter, process, process step or steps, or then-present objective to the spirit of this invention without departing from its essential teachings.

What is claimed is:
1. A compound selected from the group consisting of:
   1-(n-butylcarbamoyl)-5(6)-(3-chloropropylsulfinyl)-2-carbomethoxyaminobenzimidazole;
   1-(n-butylcarbamoyl)-5(6)-[2-(benzyloxy)ethoxy]-2-carbomethoxyaminobenzimidazole;
   1-(n-butylcarbamoyl)-5(6)-(but-3-en-1-ylthio)-2-carbomethoxyaminobenzimidazole; and
   1-(n-butylcarbamoyl)-5(6)-[2-(p-chlorophenoxy)-ethoxy]-2-carbomethoxyaminobenzimidazole;
   or a pharmaceutically acceptable salt thereof.

2. The compound of claim 1 wherein said compound is 1-(n-butylcarbamoyl)-5(6)-[2-(benzyloxy)ethoxy]-2-carbomethoxyaminobenzimidazole.

3. The compound of claim 1 wherein said compound is 1-(n-butylcarbamoyl)-5(6)-(3-chloroprop-1-ylsulfinyl)-2-carbomethoxyaminobenzimidazole.

4. The compound of claim 1 wherein said compound is 1-(n-butylcaramoyl)-5(6)-[2-(p-chlorophenoxy)ethoxy]-2-carbomethoxyaminobenzimidazole.

5. The compund of claim 1 wherein said compound is 1-(n-butylcarbamoyl)-5(6)-(but-3-en-1-ylthio)-2-carbomethoxyaminobenzimidazole.

6. A compound selected from the group of compounds represented by the formula:

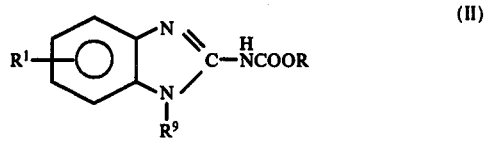

(II)

where R is lower alkyl having 1 to 4 carbon atoms; $R^1$ is $\phi\,CH_2O-(CH_2)_nO-$, n is 1 to 4, and the phenyl ring ($\phi$) of said $R^1$ moiety is optionally mono-substituted with a halo, lower alkyl, lower alkoxy, lower alkylthio, lower alkylsulfinyl, or lower alkylsulfonyl substituent; $R^9$ is $-C(O)NHR^8B^8$ is phenyl, benzyl, phenethyl or lower alkyl having 1 to 12 carbon atoms and optionally substituted with a —COOR group where R is as defined above; the $R^1$ moiety being at the 5(6)-position; or a pharmaceutically acceptable salt thereof.

7. A compound selected from the group of compounds represented by the formula:

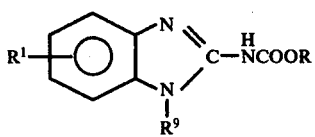
(III)

where R is lower alkyl having 1 to 4 carbon atoms; $R^1$ is $\phi$ O(CH$_2$)$_n$O where $n$ is 1 to 4 and the phenyl ring ($\phi$) of said $R^1$ moiety is mono-substituted with a halo, lower alkyl, lower alkoxy, lower alkylthio, lower alkylsulfinyl, or lower alkylsulfonyl substituent; $R^9$ is —C(O)NHR$^8$; $R^8$ is phenyl, benzyl, phenethyl or lower alkyl having 1 to 12 carbon atoms and optionaly substituted with a —COOR group where R is as defined above; the $R^1$ moiety being at the 5(6)-position; or a pharmaceutically acceptable salt thereof.

8. A composition for controlling helminths in mammals which comprises a pharmaceutically acceptable non-toxic carrier and an anthelmintically effective amount of a compound selected from the group consisting of:
  1-(n-butylcarbamoyl)-5(6)-(3-chloropropylsulfinyl)-2-carbomethoxyaminobenzimidazole;
  1-(n-butylcarbamoyl)-5(6)-2-carbomethoxyaminobenzimidazole;
  1-(n-butylcabamoyl)-5(6)-(but-3-en-1-ylthio)-2-carbomethoxyaminobenzimidazole; and
  1-(n-butylcarbamoyl)-5(6)-2-carbomethoxyaminobenzimidazole; or a pharmaceutically acceptable salt thereof.

9. The composition of claim 8 wherein said compound is 1-(n-butylcarbamoyl)-5(6)-[2-(benzyloxy)ethoxy]-2-carbomethoxyaminobenzimidazole.

10. The composition of claim 8 wherein said compound is 1-(-n-butylcarbamoyl)-5(6)-(3-chloroprop-1-ylsulfinyl)-2-carbomethoxyaminobenzimidazole.

11. The composition of claim 8 wherein said compound is 1-(n-butylcarbamoyl)-5(6)-[2-(p-chlorophenoxy)ethoxy]-2-carbomethoxyaminobenzimidazole.

12. The composition of claim 8 wherein said compound is 1-(n-butylcarbamoyl)-5(6)-(but-3-en-1-ylthio)-2-carbomethoxyaminobenzimidazole.

13. A composition for controlling helminths which comprises a pharmaceutically acceptable non-toxic carrier and an anthelmintically effective amount of a compound represented by the formula:

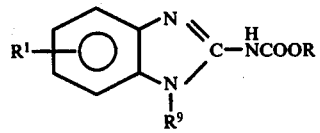
(II)

where R is lower alkyl having 1 to 4 carbon atoms; $R^1$ is $\phi$ CH$_2$O—(CH$_2$)$_n$O—, $n$ is 1 to 4, and the phenyl ring ($\phi$) of said $R^1$ moiety is optionally mono-substituted with a halo, lower alkyl, lower alkoxy, lower alkylthio, lower alkylsulfinyl, or lower alkylsulfonyl substituent; $R^9$ is —C(O)NHR$^8$; $R^8$ is phenyl, benzyl, phenethyl or lower alkyl having 1 to 12 carbon atoms and optionally substituted with a —COOR group where R is a defined above; the $R^1$ moiety being at the 5(6)-position; or a pharmaceutically acceptable salt thereof.

14. A composition for controlling helminths which comprises a pharmaceutically acceptable non-toxic carrier and an anthelmintically effective amount of a compound represented by the formula:

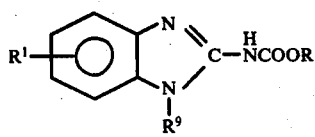
(III)

where R is lower alkyl having 1 to 4 carbon atoms; $R^1$ is $\phi$ O(CH$_2$)$_n$O where $n$ is 1 to 4 and the phenyl ring ($\phi$) of said $R^1$ moiety is mono-substituted with a halo, lower alkyl, lower alkoxy, lower alkylthio, lower alkylsulfinyl or lower alkylsulfonyl substituent; $R^9$ is —C(O)NHR$^8$; $R^8$ is phenyl, benzyl, phenethyl or lower alkyl having 1 to 12 carbon atoms and optionally substituted with a —COOR group where R is as defined above; the $R^1$ moiety being at the 5(6)-position; or a pharmaceutically acceptable salt thereof.

* * * * *